United States Patent [19]
Ring et al.

[11] Patent Number: 5,831,104
[45] Date of Patent: Nov. 3, 1998

[54] STEROID INTERMEDIATE PRODUCTS AND METHOD OF THEIR PRODUCTION

[75] Inventors: Sven Ring; Gerhard Teichmueller; Gisela Weber; Sigfrid Schwarz, all of Jena; Bernd Erhart, Kahla; Bernd Undeutsch, Jena; Harald Raethe, Jena; Peter Moellmann, Jena; Carmen Pfeiffer, Grossromstedt; Hans-Joachim Palme, Jena, all of Germany

[73] Assignee: Jenapharm GmbH, Jena, Germany

[21] Appl. No.: 303,662

[22] Filed: Sep. 9, 1994

[30] Foreign Application Priority Data

Sep. 10, 1993 [DE] Germany ............ 43 30 727.2

[51] Int. Cl.⁶ .................. C07J 1/00; C07J 21/00
[52] U.S. Cl. ............ 552/619; 540/31; 552/621; 552/646
[58] Field of Search ............ 540/31; 552/526, 552/619, 621, 646, 649

[56] References Cited

U.S. PATENT DOCUMENTS

| 5,140,106 | 8/1992 | Winterfeldt et al. | 552/607 |
| 5,364,847 | 11/1994 | Labrie et al. | 514/182 |

FOREIGN PATENT DOCUMENTS

| 0389368 | 9/1990 | European Pat. Off. |
| 0389370 | 9/1990 | European Pat. Off. |
| 2640977 | 12/1988 | France |
| 4338314C1 | 3/1995 | Germany |
| 69013957T2 | 3/1995 | Germany |
| WO87/01706 | 3/1987 | WIPO |
| WO91/11453 | 8/1991 | WIPO |

OTHER PUBLICATIONS

Schwarz, et al, *Tetrahedron*, vol. 50 (36), pp. 10709–10720, Sep. 5, 1994.
Inhibiton of Peroxidations of Lipids and . . . Journal of Physical Organic Chemistry. 1990.
Antioxidant Properties of Steroids. Mooradian, 1993.
Hydroxyestradiol–17 beta and 4–Hydroxyestradiol–17 alfa: . . . Emons, G. & Knuppen & Ball. (1981).
Comparative Properties of the Catechol Estrogene . . . Meriam, Mac–Lusky, Picard & naftolin. (1980).
The Anticonvulsiun effects of vitamin E . . . Levy, Burnham &Hwang (1991).
An Evaluation of the Anticonvulsant Effects of Vitamin E. Levy Burnham & Hwang. 1990.
Free Radical Scavenging Action of Bio–Catalyzer . . . Santiago, Osato, Hiramatsu, Edamatsu & Mori. Apr. 23, 1991.
Effects of 17Beta–Estradiol on Ciculating Adhesion Molecules. Journal of Clinical Endocrinology and Metabolism. 1994.
Chemotherapy of Arhtritis Induced in Rats . . . Newbould 1963.
A Rapid Luciferase Transfection Assy for Transcription Activation Effects and . . . Cancer Research Clinical Oncology, 1994.

*Primary Examiner*—Allen J. Robinson
*Assistant Examiner*—Barbara Badio
*Attorney, Agent, or Firm*—Michael J. Striker

[57] ABSTRACT

The invention is directed to novel steroid intermediate products of general formula I

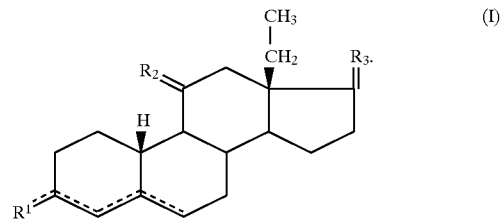

The steroid intermediate products which can be isolated according to the invention are suitable for the synthesis of 13-ethyl-11-methylene-18,19-bisnor-17α-pregn-4-en-20-in-17-ol (desogestrel).

Further, processes for producing the steroid intermediate products of general formula I are described. The olefination of the 11-oxo steroids is carried out under the influence of ultrasound.

9 Claims, No Drawings

STEROID INTERMEDIATE PRODUCTS AND METHOD OF THEIR PRODUCTION

DESCRIPTION

The invention is directed to novel steroid intermediate products of general formula I

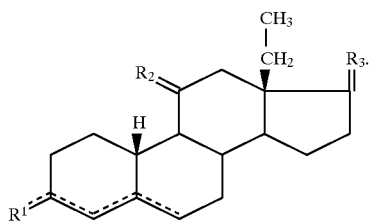

where $R^1$ represents a hydrogen atom when there are double bonds between carbon atoms 3 and 4 and carbon atoms 5 and 6 or, when there is a double bond between carbon atoms 4 and 5, $R^1$ represents two hydrogen atoms or a hydrogen atom and a hydroxy group or lower alkoxy group, $R^2$ represents a β-hydrogen atom and an α-oriented hydroxy group, $R^3$ represents an α-hydrogen atom and a β-oriented hydroxy group or where, when there is a double bond between carbon atoms 4 and 5 and $R^1$ represents two hydrogen atoms, $R^2$ and $R^3$ each represent an oxo group or $R^2$ represents an oxo group and $R^3$ represents an ethylenedioxy group or (2,2-dimethyl)trimethylenedioxy group or $R^2$ represents a methylene group and $R^3$ represents an ethylenedioxy group or a (2,2-dimethyl)trimethylenedioxy group, and to the production thereof.

The steroid intermediate products of general formula I which can be isolated by the invention are suitable for the synthesis of 13-ethyl-11-methylene-18,19-bisnor-17α-pregn-4-en-20-in-17-ol, an active ingredient known as desogestrel. Desogestrel is a gestagen which is used in hormonal contraceptives (*Drugs of Today*, XVIII (1982), 361, and *Arzneimittel-Fortschritte* [Pharmaceutical Advances] 1972 to 1985, A. Kleeman, E. Lindner and J. Engel (editors), VCH Verlagsgesellschaft, D-6940 Weinheim, pages 790,804).

The object of the present invention is to find novel steroid intermediate products of general formula I which allow a substantially more advantageous production of the active ingredient desogestrel compared with the known syntheses.

Further, the present invention has the object of developing effective, environmentally sound processes for the production of the compounds according to the invention.

According to DE 23 61 120 and DE 25 38 862, desogestrel can be isolated from 3,3,17,17-bis-ethylenedioxy-estr-5-en-11β-ol. In so doing, the starting material is transformed to 11,17-lactone by reacting with acylhypoiodite which is generated from an acylate of a heavy metal such as silver, mercury or lead and elementary iodine. The 11,17-lactone is then methylated with an organometallic compound to form the 13-acetyl-11β-hydroxy compound which is transformed into the 18a-homo-11β-hydroxy derivative. In the following synthesis steps, the 3-oxo group is eliminated from the molecule by reduction by first forming the 3-thioacetal and then degrading it with alkali metal in liquid ammonia. The 11-methylene group is introduced from the corresponding 11-oxo compound by Wittig olefination.

There are a number of disadvantages in the previously known process for synthesizing desogestrel. For example, it is necessary to form 11,17-lactone by reacting 3,3,17,17-bis-ethylenedioxy-estr-5-en-11β-ol with 1.5 to 3 molar equivalents of iodine and 2.25 to 15 molar equivalents of lead tetraacetate and to purify the reaction product by chromatography to achieve good yields. This means working with highly toxic and environmentally hazardous accessory agents such as iodine and lead compounds or mercury compounds.

Reductive elimination of the 3-oxo group from the steroid molecule by way of the 3-thioacetal first requires transforming the 3-oxo steroid to thioacetal with ethanedithiol. Ethanedithiol belongs to the class of thiol compounds characterized by a nauseating odor which is still perceptible in the ppm range.

The 11-methylene group is introduced into the target molecule by olefination of a 3-desoxo-11-oxo steroid with a high excess (a total of 6 molar equivalents) of methylene triphenylphosphoran over a long period of time (22 hours). The isolation of the reaction product inevitably results in large quantities of organophosphorus by-products which must be separated and disposed of, since it is not possible to carry out recycling at a reasonable cost.

The process is encumbered to an extreme degree in technical and economic respects in that the chemical reactions must be carried out with toxic, environmentally hazardous, ill-smelling accessory agents and by the large amounts of by-products, since the respective pollutants and by-products must not be allowed to escape and must be processed for further use or disposed of by extraordinary measures. These disadvantages of the known process for the production of desogestrel are overcome by using the compounds and process according to the invention.

The compounds of general formula I according to the invention are obtained from 18a-hydroxy steroids which can be isolated by total synthesis on an industrial scale (US-PS 3,391,170).

The 11α-hydroxy steroid of formula II

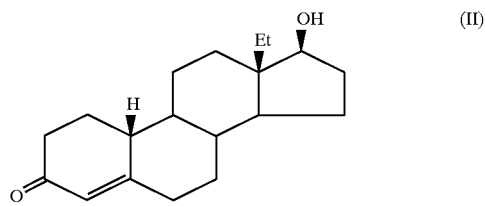

from which the compounds of general formula I according to the invention can be produced is obtained, according to UK-PS 1 128 044, from 3-methoxy-11a-homo-estra-1,3,5 (10),11-tetraen-17β-ol which is isolable by total synthesis.

Through the use of the compounds of general formula I, according to the invention, which already carry a 13-ethyl group in the ring structure, a multiple-stage process for homologizing the 13-methyl group with the inclusion of an acylhypoiodite reaction resulting in a 11,17-lactone is not required to produce desogestrel. Accordingly, there is no need for toxic and environmentally hazardous accessory agents or processes for recycling or disposing of these agents.

A further advantage of the compounds of general formula I, according to the invention, is the fact that they allow a reductive elimination of the 3-oxo group from the steroid molecule without requiring the formation of a 3-thioacetal.

The 3-oxo group can accordingly be eliminated from the steroid molecule by reduction without using ethanedithiol which is characterized by toxic stench.

A further advantage of the compounds according to the invention consists in that the reductive elimination of the 3-oxo group which is made possible by these compounds gives 3-desoxy compounds which is practically free of double bond isomers.

It is known that the reductive degradation of thioacetals derived from 4-en-3-oxo steroids results in 4-en steroids which are contaminated by 3-en steroids. Due to the structural similarity of the double bond isomers, the desired pure 4-en steroids can only be obtained at great expense, e.g., by way of dibromides (D. H. R. Barton, W. J. Rosenfelder, *J. Chem. Soc.* 1951, 1048).

The inventive principle of olefination of the 11-oxo group finally makes possible a sharp reduction in the use of the olefination agent and accordingly makes possible a reduction in the inevitable occurrence of organophosphorus by-products in that the olefination process is carried out under the influence of ultrasound.

According to the invention, the 11α-hydroxy steroid of general formula II is reduced in a manner known per se with a complex metal hydride while maintaining the trihydroxy steroid of general formula I in which there is a double bond between carbon atoms 4 and 5, where $R^1$ represents a hydrogen atom and a hydroxy group, $R^2$ represents an α-oriented hydroxy group and a β-hydrogen atom, and $R^3$ represents an α-hydrogen atom and a β-oriented hydroxy group.

The trihydroxy steroid of general formula I is reacted, in a manner known per se, with methanol in the presence of p-toluenesulfonic acid to form the methyl ether of general formula I in which there is a double bond between carbon atoms 4 and 5, $R^1$ represents a hydrogen atom and a methoxy group, $R^2$ represents a β-hydrogen atom and an α-oriented hydroxy group and $R^3$ represents an α-hydrogen atom and a β-oriented hydroxy group.

The diene steroid of general formula I, in which there is a double bond between carbon atoms 3 and 4 and carbon atoms 4 and 5, $R^1$ represents a hydrogen atom, $R^2$ represents a β-hydrogen atom and an α-oriented hydroxy group and $R^3$ represents an α-hydrogen atom and a β-oriented hydroxy group, is formed by the action of acids on the trihydroxy steroid of general formula II in which there is a double bond between carbon atoms 4 and 5, $R^1$ represents a hydrogen atom and a hydroxy group or methoxy group, $R^2$ represents a β-hydrogen atom and an α-oriented hydroxy group and $R^3$ represents an α-hydrogen atom and a β-oriented hydroxy group.

The diene steroids of general formula I or the methyl ether of general formula I is transformed with an alkali metal such as lithium or sodium or with an alkaline earth metal such as calcium in liquid ammonia, in a lower amine or in ethylenediamine to the dihydroxy steroid of general formula I in which there is a double bond between carbon atoms 4 and 5 and where $R^1$ represents two hydrogen atoms, $R^2$ represents an α-oriented hydroxy group and a β-hydrogen atom, and $R^3$ represents an α-hydrogen atom and a β-oriented hydroxy group.

The dihydroxy steroid of general formula I is formed in a manner which is known per se, e.g., with a chromium(VI) reagent or with dimethyl sulfoxide in the presence of an activator such as oxalyl chloride, sulfur trioxide pyridine complex or phosphorus(V) oxide and an amine forming the dioxo steroid of general formula I in which there is a double bond between carbon atoms 4 and 5, $R^1$ represents two hydrogen atoms and $R^2$ and $R^3$ each represent an oxo group.

Ethane-1,2-diol or (2,2-dimethyl)propane-1,3-diol and ethyl orthoformate in the presence of an acid are allowed to act upon the dioxo steroid or the dioxo steroid of general formula I is reacted with ethane-1,2-diol or (2,2-dimethyl) propane-1,3-diol I in the presence of an acid and a solvent which serves to remove the reaction liquor from the reaction mixture azeotropically to form the oxo acetals of general formula I in which there is a double bond between carbon atoms 4 and 5 and $R^1$ represents two hydrogen atoms, $R^2$ is an oxo group and $R^3$ is an ethylenedioxy group or a (2,2-dimethyl)trimethylenedioxy group.

According to the invention, the oxo acetals of general formula I are treated with 3 molar equivalents of methylene triphenylphosplhoran acted upon by ultrasound to form the methylene acetals of general formula I in which there is a double bond between carbon atoms 4 and 5 and $R^1$ represents two hydrogen atoms, $R^2$ represents a methylene group and $R^3$ is an ethylenedioxy group or a (2,2-dimethyl) trimethylenedioxy group.

The ultrasound treatment is carried out for a period of eight to ten hours at a reaction temperature of 60°-80° C. In the known Wittig olefination of 3-desoxy-11-oxo steroids to form 3-desoxy-11,11-methylene steroids with methylene triphenylphosphoran, the reaction times are 20 to 22 hours at a reaction temperature of 60° C. for which an excess of up to 8 molar equivalents of phosphoran is used. (DOS 2 361 120; A. J.v.d. Broek, et al.: *Recl. Trav. Chim.* Netherlands 94 (1975) 35).

The oxo acetals of general formula I are valuable starting materials for the production of 13-ethyl-11-methylene-18, 19-bisnor-17α-pregn-4-en-20-in-17-ol (formula IV =desogestrel) in that the acetal group is eliminated by hydrolysis and the compound of formula III is formed, which gives compound IV when reacted with lithium acetylide.

The process according to the invention is illustrated by the following formula diagram.

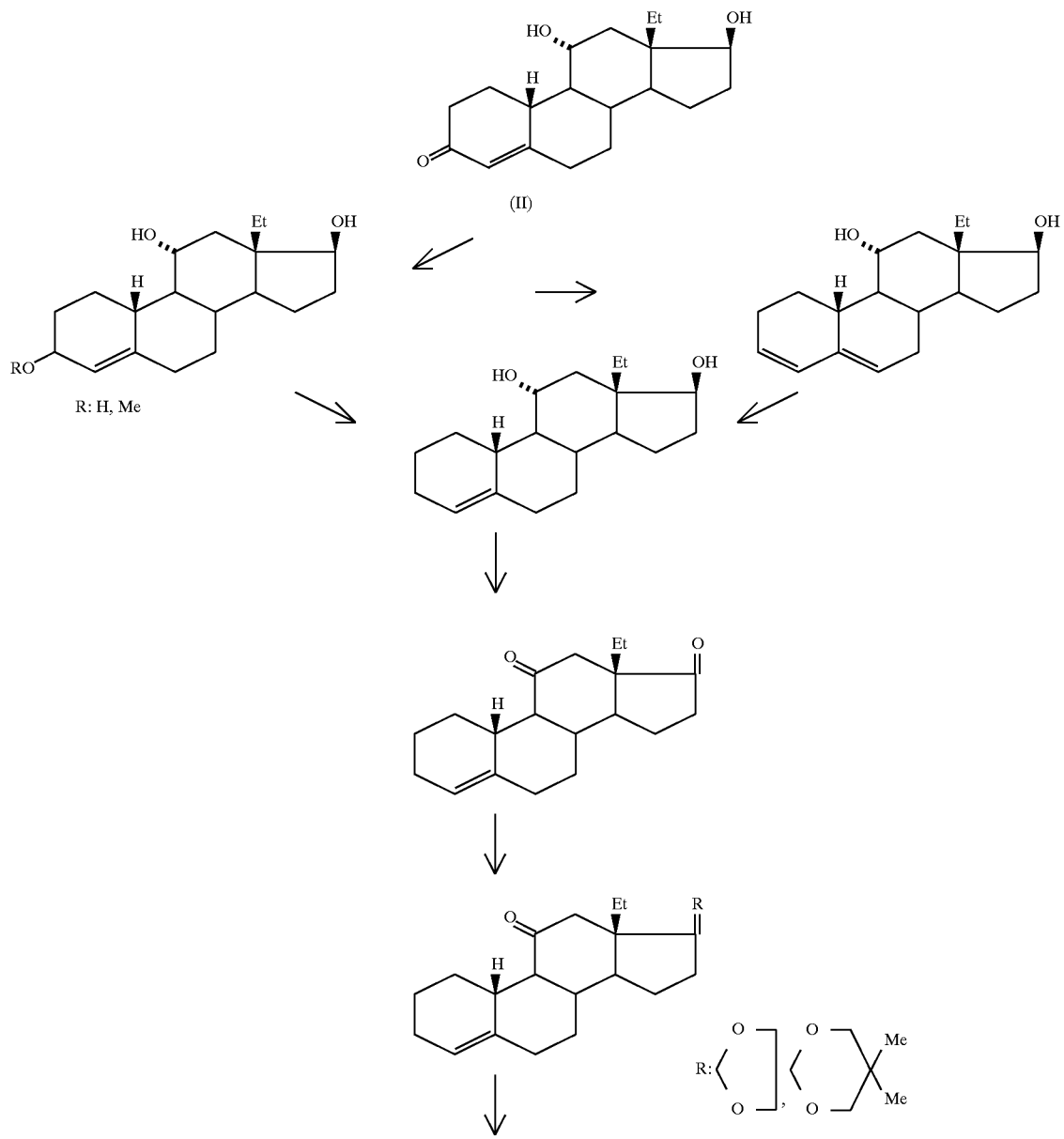

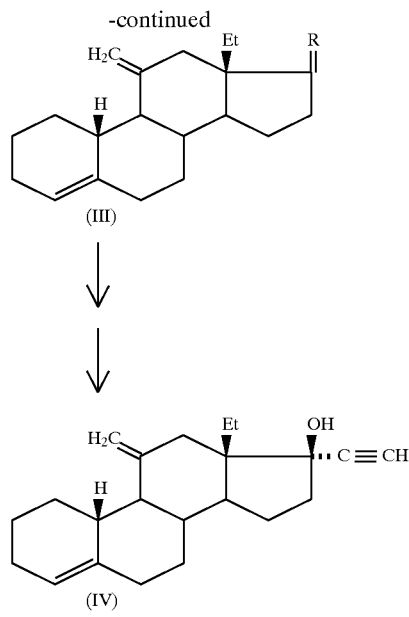

(III)

↓
↓

(IV)

DESOGESTREL

The compounds according to the invention and their production are described by way of example in the following.

EXAMPLE 1

18a-Homo-estr-4-en-3,11α,17β-triol

11α,17β-Dihydroxy-18a-homo-estr-4-en-3-one (1 g; 3.3 mmoles) and $CeCl_3 \cdot 7H_2O$ (1.26 g; 3.4 mmoles) are dissolved in methanol (10 ml). The solution is cooled to 0° C. and sodium borohydride (245 mg; 6.5 mmoles) are then added by portions. After a reaction period of 30 minutes, the mixture is neutralized with aqueous acetic acid (50-percent) and the solution is extensively evaporated under vacuum. The residue is distributed between water and ethyl acetate. The organic phase is washed with saturated aqueous sodium chloride solution, dried over anhydrous sodium sulfate and evaporated under vacuum until dry. The 18a-homo-estr-4-en-3,11α,17β-triol is obtained as a foam which can be used in the next step. The 18a-homo-estr-4-en-3α,11α,17β-triol with a melting point of 180° C. to 185° C. and 18a-homo-estr-4-en-3β,11α,17β-triol with a melting point of 133.5° C. to 138° C. are obtained by chromatography on silica gel with ethyl acetate as eluant.

EXAMPLE 2

3-Methoxy-18a-homo-estr-4-en-,11α,17β-diol

18a-Homo-estr-4-en-3,11α,17β-triol (1 g; 3.3 mmoles) is dissolved in methanol and p-toluenesulfonic acid (10 mg; 0.06 mmole) is added to the solution. The mixture is allowed to stand for 1 hour at room temperature. Aqueous saturated sodium hydrogen carbonate solution (0.5 ml) is then added and the methanol is distilled off under vacuum. The residue is absorbed in ethyl acetate and the organic phase is washed with aqueous saturated sodium chloride solution and dried over anhydrous sodium sulfate. After evaporating until dry, 3-methoxy-18a-homo-estr-4-en-11α,17β-diol is obtained as foam which can be used in the next step. 3α-Methoxy-18a-homo-estr-4-en-11α,17β-diol with a melting point of 150° C. to 154° C. and 3β-methoxy-18a-homo-estr-4-en-11α, 17β-diol with a melting point of 100° C. to 106° C. are obtained by chromatography on silica gel with ethyl acetate as eluant.

EXAMPLE 3

18a-Homo-estra-3,5-dien-,11α,17β-diol

18a-Homo-estr-4-en-3,11α,17β-triol (770 mg; 2.5 mmoles) and p-toluenesulfonic acid (140 mg; 0.8 mmole) are dissolved in methanol (7 ml). The solution is heated for 2 hours at +50° C. and is then cooled to room temperature, neutralized with aqueous saturated sodium hydrogen carbonate solution and extensively evaporated under vacuum. Water is added to the residue and a crystalline precipitate is obtained which is removed by suction, dried and recrystallized from methanol. 18a-Homo-estra-3,5-dien-11α,17β-diol with a melting point of 145° C. to 148° C. is obtained. The same compound is obtained when starting from 3-methoxy-18a-homo-estr-4-en-11α, 17β-diol.

EXAMPLE 4

18a-Homo-estr-4-en-11α,17β-diol a) From 3-methoxy-18a-homo-estr-4-en-11α,17β-diol A solution of 3-methoxy-18a-homo-estr-4-en-11α,17β-diol (120 g; 0.37 mol) in tetrahydrofuran (240 ml) is added dropwise to a mixture of ethylamine (1032 ml) and lithium (11.44 g; 1.65 g-atom) in such a way that the reaction temperature does not exceed +10° C. A post-reaction is then allowed to take place for up to an additional hour. The reaction mixture is then decomposed by careful addition of ammonium chloride (90 g) and the ethylamine is extensively distilled off under mild conditions. The residue is absorbed in tetrahydrofuran, the tetrahydrofuran solution is repeatedly extracted with alkaline lye and then evaporated under vacuum. The distillation residue is mixed with methyl tert-butyl ether and crystallized. The yielded crystalline product is collected by suction, washed with a little cold methyl tert-butyl ether and then dried. The obtained crystalline product is recrystallized from toluene. 18a-Homo-estr-4-en-11α,17β-diol with a melting point of 118.5° C. to 121° C. is obtained.

b) From 18a-homo-estra-3,5-dien-11α,17β-diol

Sodium (440 mg; 0.019 g-atom) is added to a mixture of ammonia (35 ml), 18a-homo-estra-3,5-dien-11α,17β-diol (1.4 g; 4.85 mmoles), tetrahydrofuran (25 ml) and isopropanol (1 ml) at temperatures below −46° C. After a total reaction time of two hours, the reaction mixture is decomposed by adding ammonium chloride (1 g). The ammonia is distilled off and the residue is worked up by adding water (20 ml) and concentrated alkaline lye. After separating the aqueous phase, the tetrahydrofuran solution is evaporated until dry in a rotary vacuum evaporator. After cleaning over bis-trimethylsilyl ether and recrystallizing from toluene, 18a-homo-estr-4-en-11α,17β-diol with a melting point of 119° C. to 121° C. is obtained.

EXAMPLE 5

18a-Homo-estr-4-en-3,17-dione a) 18a-Homo-estr-4-en-11α,17β-diol (1 g; 3.44 mmoles) is dissolved in acetone (6 ml) and mixed with 8N-chromicsulfuric acid (3 ml) at 0° C. The mixture is stirred for 3 hours at 0 C., water (100 ml) is added and the acetone is distilled off under vacuum. After suction filtration and washing with water, 18a-homo-estr-4-en-3,17-dione with a melting point of 151° C. to 153° C. is obtained.

b) 18a-Homo-estr-4-en-11α,17β-diol (10 g; 34.4 mmoles) is dissolved in triethylamine (40 ml; 288 mmoles) and dimethyl sulfoxide (34.7 ml; 488 mmoles). Sulfur trioxide pyridine complex (20 g; 126 mmoles) is then added while stirring at room temperature. The reaction mixture is stirred for another 3 hours at room temperature and then diluted with water (250 ml). Extraction is carried out with toluene (3×50 ml), the collected extracts are washed with saturated aqueous sodium chloride solution, dried with anhydrous sodium sulfate and evaporated under vacuum. Recrystallizing the residue from methanol yields 18a-homo-estr-4-en-3,17-dione with a melting point of 154° C. to 155° C.

EXAMPLE 6

17,17-Ethylenedioxy-18a-homo-estr-4-en-11-one

18-Homo-estr-4-en-11,17-dione (1 g; 3.49 mmoles), ethylene glycol (1 ml; 17.9 mmoles), triethyl orthoformate (2 ml; 12.0 mmoles) and p-toluenesulfonic acid (0.06 g; 0.315 mmole) are stirred together at 40° C. After 5 hours, the mixture is diluted with toluene (100 ml) and the solution is washed with 5-percent aqueous sodium hydrogen carbonate solution (6×50 ml), dried over anhydrous sodium sulfate and reduced. The residue is recrystallized from ethyl acetate/n-hexane yielding 17,17-ethylenedioxy-18a-homo-estr-4-en-11-one with a melting point of 98° C. to 100° C.

EXAMPLE 7

17,17-(2,2-dimethyl)trimethylenedioxy-18a-homo-estr-4-en-11-one

18a-Homo-estr-4-en-11,17-dione (1 g; 3.49 mmoles), 2,2-dimethylpropane-1,3-diol (1 g; 9.60 mmoles), triethyl orthoformate (2 ml; 12 mmoles) and p-toluenesulfonic acid (0.06 g; 0.315 mmole) are stirred together at 40° C. After 6 hours, the precipitate is collected by suction and washed with cold ethanol (5 ml; 0° C.). 17,17-(2,2-Dimethyl) trimethylenedioxy-18a-homo-estr-4-en-11-one with a melting point of 127° C. to 130° C. is obtained.

EXAMPLE 8

11-Methylene-18a-homo-estr-4-en-17-one a) Absolute toluene (1.2 l), methyltriphenylphosphonium iodide (1.18 kg; 2.92 moles), sodium hydride 80-percent (86.5 g; 2.88 moles) and absolute dimethyl sulfoxide (1.6 l) are added one after the other in a protective argon gas atmosphere with exclusion of moisture to a 6-liter reaction vessel which is arranged in an ultrasonic bath (25 kHz). The irradiation is started and the mixture is heated to +70° C. After hydrogen development is concluded, a solution of 17,17-ethylenedioxy-18a-homo-estr-4-en-11-one (317.4 g; 0.96 moles) in toluene (400 ml) is added to the ylide solution. Irradiation is continued for 8 to 10 hours while maintaining a reaction temperature of +70° C. First the toluene in its entirety and then the dimethyl sulfoxide (approximately 0.51 l) are distilled off from the reaction mixture under vacuum. The distillation residue is cooled to +30° C. and carefully decomposed while stirring with water (1.5 l). The resulting solution is extracted with cyclohexane (3×11), the collected extracts are washed with water (2×11), reduced to a volume of 1.5 l, filtered over neutral aluminum oxide (500 g) and evaporated under vacuum. The residue consists of 17,17-ethylenedioxy-11-methylene-18a-homo-estr-4-en. This residue is dissolved in a 1:1mixture of ethyl acetate and methanol, to which is added p-toluenesulfonic acid hydrate (10 g) while stirring. Stirring is continued for 2 additional hours at room temperature and saturated aqueous sodium hydrogen carbonate solution is added to this mixture until neutralized and the organic phase is separated. After evaporation under vacuum, the residue is crystallized from methanol and 11-methylene-18a-homo-estr-4-en-17-one with a melting point of 101° C. to 102.5° C. is obtained. (DOS 2 361 120: 96° C. to 99° C.).

b) 17,17-(2,2-dimethyl)trimethylenedioxy-18a-homo-estr-4-en-11-one (36 g; 96 mmoles) is olefinated with the methyltriphenylphosphonium iodide (118 g; 0.292 mmole) and sodium hydride 80-percent (6.65 g; 0.288 mole) in dimethyl sulfoxide/toluene (160 ml/120 ml) as in Example 10 and the formed 11-methylene acetal is eliminated by hydrolysis to yield 11-methylene-18a-homo-estr-4-en-17-one which is identical to the compound obtained in Example 8a.

EXAMPLE 9

Acetylene was passed into a solution of lithium (10 g; 1.44 g-atom) in ethylenediamine (200 ml) for 2 hours. A solution of 11-methylene-18a-homo-estr-4-en-17-one (10 g; 35 mmoles) in tetrahydrofuran (100 ml) is then added, followed by stirring for 2 hours at a reaction temperature of +25° C. with further introduction of acetylene. The solution is then diluted with ethyl acetate (250 ml) and neutralized with sulfuric acid (20-%) accompanied by cooling. After the working up of the organic phase, chromatography of the product on silica gel (eluant: dichloromethane) and recrystallization of the purified compound from n-hexane, desogestrel with a melting point of 109° C. to 111 C. is obtained (DOS 2 361 120: 109° C. to 110° C.).

We claim:

1. A steroid compound of the formula II'

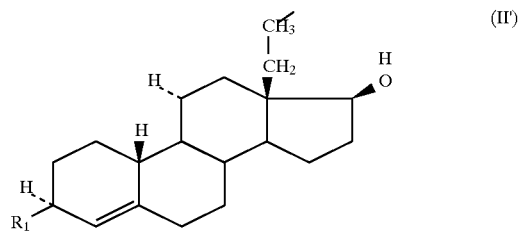

(II')

wherein $R_1$ represents OH or a methoxy group.

2. A steroid compound of the formula III'

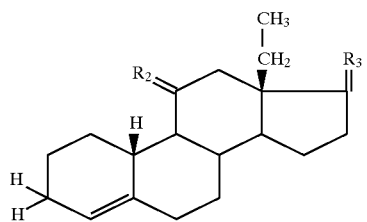

wherein $R_2$ represents an oxo or methylene group and $R_3$ represents an oxo group, an ethylenedioxy or a (2,2-dimethyl)trimethylenedioxy group when $R_2$ is an oxo group and R3 represents an ethylenedioxy or (2,2-dimethyl)trimethylenedioxy group when $R_2$ is a methylene group.

3. 18a-homo-estr-4-en-3,11α,17β-triol.
4. 3-methoxy-18a-homo-estr-4-en-11α,17β-diol.
5. 18a-homo-estra-3,5-dien-11α,17β-diol.
6. 18a-homo-estr-4-en-3,17-dione.
7. 17,17-ethylenedioxy-18a-homo-estr-4-en-11-one.
8. 17,17-(2,2-dimethyl)trimethylenedioxy-18a-homo-estr-4-en-11-one.
9. 17,17-(2,2-dimethyl)trimethylenedioxy-11-methylen-18a-homo-estr-4-en.

* * * * *